(12) United States Patent
Figulla et al.

(10) Patent No.: US 7,198,646 B2
(45) Date of Patent: Apr. 3, 2007

(54) DEVICE FOR FASTENING AND ANCHORING CARDIAC VALVE PROSTHESES

(75) Inventors: Hans-Reiner Figulla, Jena (DE); Markus Ferrari, Jena (DE); Carsten Weber, Jena (DE); Thomas Peschel, Jena (DE); Christoph Damm, Jena (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 10/204,990

(22) PCT Filed: Feb. 28, 2001

(86) PCT No.: PCT/DE01/00837

§ 371 (c)(1),
(2), (4) Date: Nov. 25, 2002

(87) PCT Pub. No.: WO01/62189

PCT Pub. Date: Aug. 30, 2001

(65) Prior Publication Data

US 2003/0149478 A1    Aug. 7, 2003

(30) Foreign Application Priority Data

Feb. 28, 2000    (DE) ................................ 100 10 074

(51) Int. Cl.
*A61F 2/06*    (2006.01)
*A61F 2/24*    (2006.01)

(52) U.S. Cl. ...................................... 623/900; 623/1.15

(58) Field of Classification Search ........ 623/2.1–2.34, 623/1.5–1.54, 900, 1.15–1.19, 1.24, 1.26
See application file for complete search history.

(56) References Cited

U.S. PATENT DOCUMENTS

| 5,234,456 | A | * | 8/1993 | Silvestrini | .................... | 623/1.2 |
| 5,342,348 | A | * | 8/1994 | Kaplan | .................... | 604/891.1 |
| 5,411,552 | A | | 5/1995 | Anderson et al. | | |
| 5,476,508 | A | * | 12/1995 | Amstrup | ..................... | 623/1.2 |
| 6,146,417 | A | | 11/2000 | Ischinger | | |
| 6,245,102 | B1 | * | 6/2001 | Jayaraman | .................. | 623/1.15 |
| 6,425,916 | B1 | * | 7/2002 | Garrison et al. | ........... | 623/2.11 |
| 6,626,939 | B1 | * | 9/2003 | Burnside et al. | ........... | 623/1.38 |
| 6,773,455 | B2 | * | 8/2004 | Allen et al. | ................. | 623/1.15 |
| 2001/0039450 | A1 | * | 11/2001 | Pavcnik et al. | | |
| 2002/0111668 | A1 | * | 8/2002 | Smith | ........................ | 623/1.13 |

FOREIGN PATENT DOCUMENTS

| DE | 196 33 901 A1 | 2/1998 |
| DE | 198 57 887 A1 | 7/2000 |

* cited by examiner

*Primary Examiner*—Corrine McDermott
*Assistant Examiner*—Cheryl Miller
(74) *Attorney, Agent, or Firm*—Barnes & Thornburg

(57) ABSTRACT

This invention relates to a device for fastening and anchoring heart valve prostheses which is essentially formed of wire-shaped interconnected elements. The aim of the invention is to be able to be implant, in a minimally invasive manner, a device of this type via the aorta by compressing the device to make it smaller, and by extending the same at the site of implantation, whereby ensuring a secure retention and a secure sealing with regard to the aorta wall. To this end, the invention provides that for fastening and supporting a cardiac valve prosthesis, three identical pairs of arched elements are interconnected, with a configuration that is offset by 120°, by means of solid body articulations. These solid body articulations carry out the function of pivot bearings.

11 Claims, 1 Drawing Sheet

DEVICE FOR FASTENING AND ANCHORING CARDIAC VALVE PROSTHESES

CROSS-REFERENCE TO RELATED APPLICATIONS

This application is a U.S. national counterpart application of international application serial no. PCT/DE01/00837 filed Feb. 28, 2001, which claims priority to German application serial No. 100 10 074.0 filed Feb. 28, 2000.

BACKGROUND AND SUMMARY OF THE INVENTION

The invention relates to a device for fastening and anchoring cardiac valve prostheses which is essentially formed of wire-shaped interconnected elements. In the folded up state it is allowed to be introduced through the aorta in a minimally invasive manner, and be anchored in the aorta wall after being deployed such that the implanted and secured heart valve prosthesis is allowed to adopt the function of the endogenous heart valve.

Heretofore, it did not succeed in a satisfactory extent to suggest a solution wherein both a secure sealing against the aorta wall and a secure retention can be ensured. On that occasion, such a device or such an anchoring support (stent) must be able to be folded up small enough in order to be stretched then at the site of implantation. With the known solutions a satisfactory enlargement will not be achieved with the appropriate tension force which is allowed to ensure such a retention. Proposals in which a form storage metal (memory metal) is to be used as well do not meet the requirements although an expansion takes place with these materials when a transition temperature has been reached and exceeded, respectively.

The solution as described in U.S. Pat. No. 5,411,552 cannot meet the requirements as well since a relatively instable object is to be used.

Another problem which is solved in an unsatisfactory manner so far is the secure attachment of an artificial or biological heart valve prosthesis. As a rule, the prostheses are lavishly sewn on to a stent. This is time-consuming and has to be carried out with great care in order to avoid damages.

Since the implanted heart valve prostheses have to be able to function over long periods the constructional design plays an essential role as well since damages and leakages can occur after the implantation otherwise which can result in life threatening states of the patient.

Hence, it is an object of the invention to suggest a device for fastening and anchoring heart valve prostheses which can be folded up small enough, and deployed at the site of implantation for a minimally invasive implantation through the aorta wherein a secure retention and a secure sealing with respect to the aorta wall are ensured.

According to the invention this object is solved with a device according to claim 1.

Advantageous embodiments and improvements of the invention can be achieved with the features mentioned in the subclaims.

Three identical pairs of arched elements each are substantial elements of the solution according to the invention which are interconnected in a configuration that is offset by 120°. The two arched elements of one pair are bent opposite to each other in a curved manner and connected by means of solid articulations. The solid articulations simultaneously meet the function of pivot bearings about which the arched elements of one pair can be swivelled similarly as with a seesaw. If a pressure force is exerted upon one of the arched elements, e.g. through the peristaltic action of the aorta, this arched element will be swivelled according to the same direction about the axis of rotation on the solid articulation. Simultaneously, the respective other arched element of the pair will be swivelled opposite thereto. Therefore, one of the two arched elements of the pair is then already pressed against the aorta wall increasing the sealing and the retention.

It is favourable to dimension the arched elements of a pair such that as far as possible the same lever relations are met with respect to the solid articulations forming the pivot bearings, thus rocker arms with an identical length or at least with approximately the same length will be formed.

The relative great distances of the solid articulations predetermined by the configuration of 120° of the pairs of arched elements, and the large surface areas covered by the arched elements as well are also advantageous wherein the distal arched elements do not only serve for fastening the heart valve prosthesis but also adopt a supporting function.

The mentioned advantages can still be improved by means of another curved arched element which is arranged in the distal direction.

On that occasion, the second distal arched element in its distal area is designed in a curved manner approximately like the first distal arched element. Partly, these two arched elements are designed and shaped such that they pass adjacent to each other, and gaps are formed between them. They are allowed to be interconnected at the same place at which the solid articulations are also arranged as a connection toward the arched element curved in the proximal direction. Hence, the formed gaps are open in the distal direction, and portions of the heart valve prosthesis are allowed to be introduced into the gaps and be supported.

At least one portion of a distal arched element is proximally retracted and guided up to a turning point in which adjacent arched elements are collected. With two distally arranged arched elements this applies to the respective distally outer arched element.

For stiffening and as a further possibility of fastening the heart valve prosthesis it is allowed to use an angular curved arched element being proximally retracted as well, the curved portions of which are located between the respective adjacent arched elements and are formed partly following the respective curvature. These arched elements with the distal ends thereof are secured to the one distally outer arched element or the respective distally outer arched element. Herein, the attachment also forms a respective solid articulation. These should still be located in a distance to the other solid articulations connecting one pair.

With a device being implanted and stretched over the pockets of a heart valve prosthesis then can be pushed in, held and supported there.

The construction of the arched element of the device according to the invention supports a heart valve prosthesis in a large-surface manner, and therefore with care. Additionally, it is allowed to be fastened with a substantially lower amount, for example by sewing.

The constructional solution enables a secure retention and the required sealing on the aorta wall, and with respect thereto, respectively. Pressing against the heart valve prosthesis from the inside by means of the arched element is advantageous for the sealing and for a reduced load of the heart valve prosthesis.

The device according to the invention can be implanted by means of a balloon catheter and can be deployed at the site of implatation. Advantageously, for the device is used a form storage metal as well having a suitable transition temperature by means of which an extension can be additionally achieved. For this, an alloy containing nickel and titanium can be employed which is available under the designation of Nitinol.

Moreover, the portion of the device supporting and holding the heart valve prosthesis can be implanted separately to a supporting body which is still referred to hereinafter with the description of an embodiment without reducing the advantageous properties. The implantation of this portion substantially consisting of the three segments having the heart valve prosthesis attached thereto then can operatively take place in a conventional form.

In the text that follows, the invention will be explained in more detail according to an embodiment in which

DETAILED DESCRIPTION OF THE DRAWINGS

Figure 1:
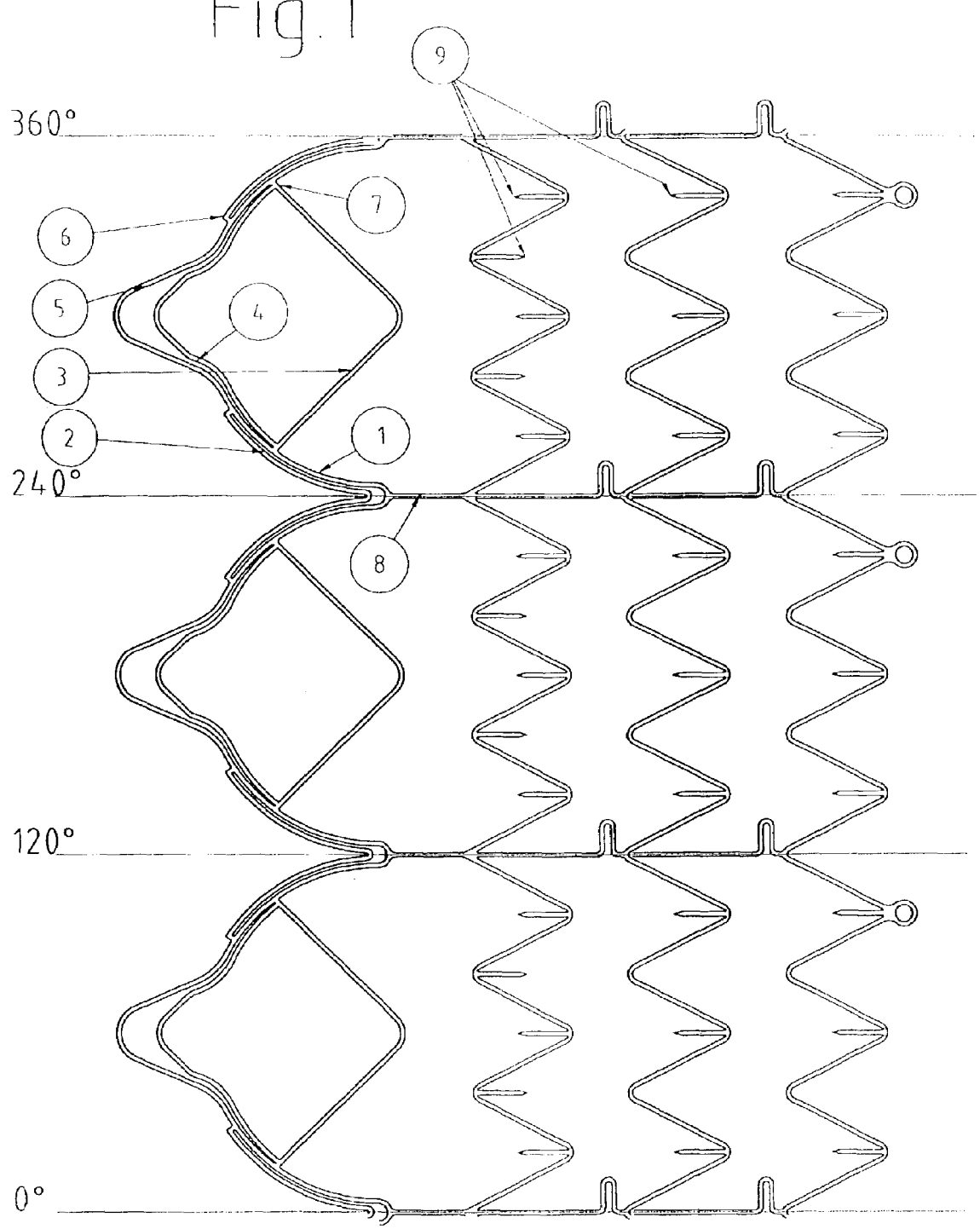
FIG. 1 shows a developed view of an embodiment of a device according to the invention.

In FIG. 1 is shown a developed view of an embodiment of a device according to the invention. The device is radially symmetrically designed wherein three identical portions are used in a configuration of 120°.

Each portion uses an arched element construction as a carrier and for fastening an artificial or biological heart valve prosthesis.

With this embodiment two arched elements 4 and 5 are used which are distally arranged outside wherein the outer arched element 5 could be abandoned as the case may be.

The arched element 4 bent into a curved manner is connected to an arched element 3 which is bent in the opposite direction. The two sided connections represent solid articulations 7 which simultaneously adopt pivot functions for the two arched elements 3 and 4 representing levers as it is already described in the general part of the description.

The second arched element 3 which is outwardly bent and distally arranged increases the stability and offers an additional supporting and fastening possibility for the heart valve prosthesis. On that occasion, the two distally outer arched elements 4 and 5 are interconnected as well, wherein this connection is allowed to occur at the same place at which the solid articulations 7 are also arranged.

There are gaps between the two arched elements 4 and 5 which are open from the distal direction into which the portions of the heart valve prosthesis can be introduced and fixed there.

The arched element 5 being the outer one here is further inwardly pulled in the proximal direction, and is connected with its end to a respective supporting ridge 8. In this embodiment, the supporting ridges 8 are aligned in parallel to the longitudinal axis of the device, and together with saw tooth shaped, rhombic or meander shaped transversal ridges they form a supporting body which in the deployed state closely fits on the aorta wall. For interlocking, additional tips 9 can be present and designed, respectively, on the supporting ridges 8, and/or the transversal ridges which interlock in the aorta wall.

The configuration and length of the supporting ridges 8, and the respective great distance toward the heart valve prosthesis fastened in the area of the arched elements 3, 4 and 5 enable positioning the heart valve prosthesis without locking and covering the coronary vessels, respectively.

With the embodiment as shown herein, additional arched elements 2 being proximally pulled in are present between the individual segments used in a configuration of 120° which are connected to the distally outer arched elements 5. Herein, the connections are solid articulations 6 as well, however, which should be arranged in a distance toward the solid articulations 7 as far as possible. Thus, two levers per segment can be used, and forces twice as large can be realized with such a double-reflected structure in order to fix the device.

In the deployed implanted state the portions of the heart valve prosthesis can be mutually introduced in turn between the portions 1 of the arched elements 5 and the arched elements 2, thus being supported and fixed thereto.

The number of the arched elements used can still be increased, however, to improve the retention and to further decrease the load of the heart valve prosthesis.

The invention claimed is:

1. A device for fastening and anchoring a heart valve prosthesis, the device consisting of three identical sections, each section being coupled to adjacent sections on each side of said section by an elongated supporting ridge extending in a direction generally parallel to a longitudinal axis of the device, each section having a first arched element arched in a first direction, a second arched element arched in the first direction, and a third arched element arched in a second direction opposite from the first direction, the second and third arched elements being coupled to the first arched element at first points to define between the first and second arched elements a first space, each section further comprising a fourth arched element arched in the second direction and having ends coupled to the first arched element of said section and a first arched element of an adjacent section at second points distinct from the first points to define between the fourth arched element and the adjacent first arched elements a second space.

2. A device for supporting a heart valve prosthesis, the device consisting essentially of three substantially identical elements, each element being coupled to adjacent elements on each side of said element by an elongated supporting member extending in a direction generally parallel to a longitudinal axis of the device, each element including a first arched member coupled to, and extending in a first direction generally away from said first arched member's respective supporting members, and a second arched member coupled to the first arched member at points different from the first arched member's coupling to its respective supporting members, the second arched member extending generally in a second direction opposite from the first direction, wherein each element further includes a third arched member coupled to the first arched member at substantially the same points as the second arched member is coupled to the first arched member, the third arched member extending generally in the first direction, each element further including a pair of fourth arched members, each of said fourth arched members extending alongside, and conforming generally to, the curvature of a portion of the first arched member, each of the fourth arched members being coupled to a first arched member intermediate opposite ends of said first arched member and extending from said coupling to said first arched member generally in said second direction toward a respective supporting member.

3. The device of claim 2 wherein each fourth arched member extends to a point adjacent a respective supporting member, turns, and extends generally in the first direction, conforming generally to the curvature of a portion of a first arched member of an adjacent element on one side of said element.

4. The device of claim 3 wherein each element further includes transversal members extending between its respective supporting members.

5. The device of claim 4 wherein at least some of said transversal members include tips to facilitate anchoring of said device into tissue of a vessel or the heart of a wearer of the device.

6. The device of claim 4 constructed from memory metal.

7. The device of claim 3 constructed from memory metal.

8. The device of claim 2 wherein each element further includes transversal members extending between its respective supporting members.

9. The device of claim 8 wherein at least some of said transversal members include tips to facilitate anchoring of said device into tissue of a vessel or the heart of a wearer of the device.

10. The device of claim 8 constructed from memory metal.

11. The device of claim 2 constructed from memory metal.

* * * * *